US005888727A

United States Patent [19]
Lund et al.

[11] Patent Number: 5,888,727
[45] Date of Patent: Mar. 30, 1999

[54] METHOD OF INHIBITION OF NUCLEO-CYTOPLASMIC TRANSPORT BY M PROTEIN OF VESICULAR STOMATITIS VIRUS

[75] Inventors: Elsebet Lund; James E. Dahlberg; Lu-Shiun Her, all of Madison, Wis.; Yan Cheng, San Francisco, Calif.; Christian Grimm, Naenikon/Greifense, Switzerland

[73] Assignee: Wisconsin Alumni Research Foundation, Madison, Wis.

[21] Appl. No.: 861,104

[22] Filed: May 21, 1997

Related U.S. Application Data

[60] Provisional application No. 60/018,621, May 23, 1996.
[51] Int. Cl.[6] .............................. C12Q 1/68; C12Q 1/70; C12N 5/10; C07H 21/02
[52] U.S. Cl. .................................... 435/5; 435/6; 435/7.1; 435/7.2; 435/325; 435/375; 435/455; 536/23.1; 536/23.72; 536/24.1
[58] Field of Search .......................... 435/5, 6, 7.1, 172.1, 435/172.3, 375, 7.2, 325, 366, 455; 536/23.1, 23.72, 24.1; 424/185.1, 224.1, 93.2, 93.6; 514/2

[56] References Cited

PUBLICATIONS

Orken et al., "Report and Recommendations of the Panel to Assess the NIH Investment in Research on Gene Therapy" Dec. 9, 1995.
Gorlich et al., Science, vol. 271, pp. 1513–1518, Mar. 15, 1996.
Verma et al., Nature, vol. 389, pp. 239–242, Sep. 18, 1997.
Her et al., Science, vol. 276, pp. 1845–1848, Jun. 20, 1997.
B.L. Black, et al., "The Role of Vesicular Stomatitis Virus Matrix Protein in Inhibition of Host–Directed Gene Expression is Genetically Separable from its Function in Virus Assembly," *J. Virol.* 67(8) :4814–4821, 1993.
Y. Cheng, et al., "Diverse Effects of the Guanine Nucleotide Exchange Factor RCC1 on RNA Transport," *Science* 267:1807–1810, 1995.

D.E. Crone and J.D. Keene, "Viral Transcription is Necessary and Sufficient for Vesicular Stomatitis Virus to Inhibit Maturation of Small Nuclear Ribonucleoproteins," *J. Virol.* 63(10) :4172–4180, 1989.
C. Featherstone, et al., "A Monoclonal Antibody Against the Nuclear Pore Complex Inhibits Nucleotcytoplasmic Transport of Protein and RNA In Vivo," *J. Cell Biol.* 107:1289–1297, 1988.
L.D. Fresco, et al., "Rapid Inhibition of Processing and Assembly of Small Nuclear Ribonucleoproteins after Infection with Vesicular Stomatitis Virus," *Molec. Cell. Biol.* 7(3):1148–1155, 1987.
D. Görlich and I.W. Mattaj, "Protein Kinesis: Nucleocytoplasmic Transport," *Science* 271:1513–1518, 1996.
C. Grimm, et al., "In vivo Selection of RNAs that Localize in the Nucleus," *EMBO J.* 16(4) :793–806, 1997.
C. Grimm, et al., "Selection and Nuclear Immobilization of exportable RNAs," *Proc. Natl. Acad. Sci. USA* 94:10122–10127, 1997.
E. Izaurralde and I.W. Mattaj, "RNA Export," *Cell* 81:153–159, 1995.
S.–Y. Paik, et al., "Inducible and Conditional Inhibition of Human Immunodeficiency Virus Proviral Expression by Vesicular Stomatitis Virus Matrix Protein," *J. Virol.* 69(6):3529–3537, 1995.
M.A. Powers, et al., "The Vertebrate GLFG Nucleoporin, Nup98, Is an Essential Component of Multiple RNA Export Pathways," *J. Cell Biol.* 136(2):241–250, 1997.
C. Tuerk and L. Gold, "Systematic Evolution of Ligands by Exponential Enrichment: RNA Ligands to Bacteriophage T4 DNA Polymerase," *Science* 249:505–510, 1990.

*Primary Examiner*—David Guzo
*Attorney, Agent, or Firm*—Quarles & Brady LLP

[57] ABSTRACT

A method of inhibiting transport of nucleic acids between the nucleus and cytoplasm of a cell is disclosed. In one embodiment, this method comprises the step of exposing a cell to a sufficient amount of vesicular stomatitis virus M protein such that the transport of RNA and protein through the nuclear envelope of the cell is impeded. A chimeric RNA capable of nuclear export is also disclosed.

17 Claims, 1 Drawing Sheet

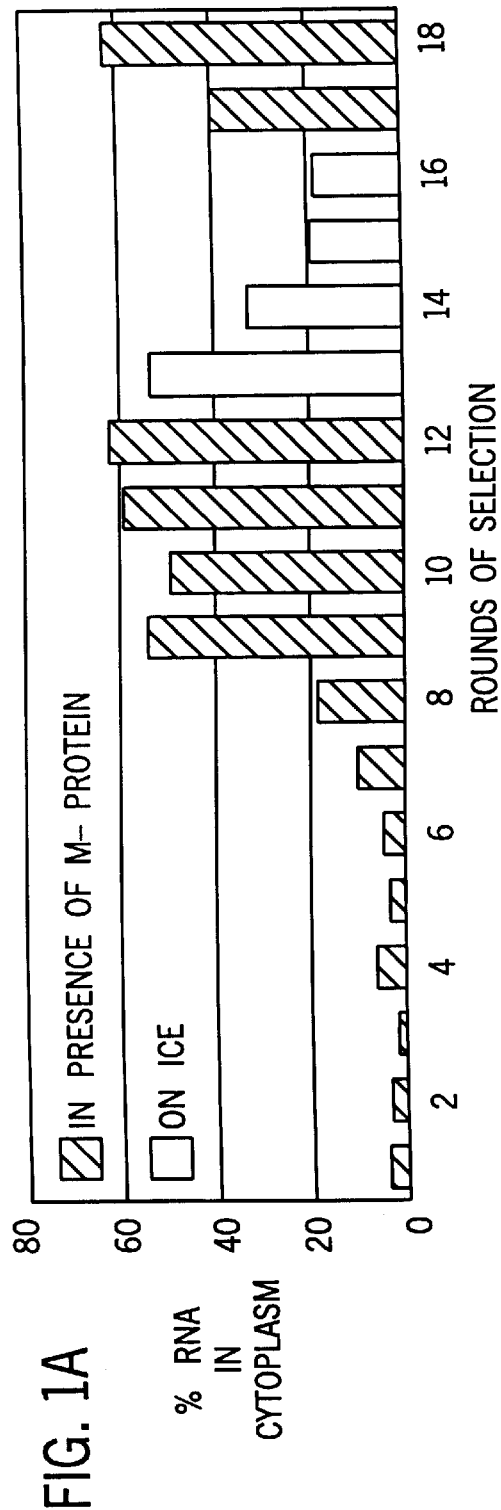

METHOD OF INHIBITION OF NUCLEO-CYTOPLASMIC TRANSPORT BY M PROTEIN OF VESICULAR STOMATITIS VIRUS

STATEMENT REGARDING FEDERALLY SPONSORED RESEARCH OR DEVELOPMENT

This invention was made with United States government support awarded by the following agencies: NIH Grant No. GM30220. The United States has certain rights in this invention.

CROSS-REFERENCE TO RELATED APPLICATION

This application claims priority to U.S. Ser. No. 60/018, 621, filed on May 23, 1996 which is incorporated by reference herein as if fully set forth.

BACKGROUND OF THE INVENTION

The transport of macromolecules through the nuclear envelope is a complex process that involves many protein factors and an energy source such as GTP (see E. Izaurralde and I.W. Mattaj, Cell 81:153, 1995 and D. Gorlich, et al., Science 271:1513, 1996 for review). Besides the many components of the nuclear pore complex (NPC), several soluble proteins localized to one or both sides of the nuclear envelope are also essential. Key to this process are the nucleotide GTP, a GTPase (Ran) and the nuclear GTP:GDP exchange factor RCC1. We showed previously that RCC1, which is required for export of some messenger RNAs (mRNAs), is also required for export of precursors of small nuclear RNAs (pre-snRNAs) and ribosomal RNAs (rRNAs) but not for that of transfer RNAs (tRNAs). Because pre-snRNAs undergo maturation in the cytoplasm, this inhibition resulted in accumulation of immature RNAs in nuclei.

Keene and coworkers had previously shown that infection of cells by the cytoplasmically replicating negative strand vesicular stomatitis virus (VSV) resulted in inhibition of processing of pre-snRNAs. The similarities between inactivation of the RCC1-dependent export pathway and VSV infection, with respect to accumulation of unprocessed pre-snRNAs, led us to ask if VSV infection might inhibit export of these RNAs from the nuclei of infected cells.

Two VSV gene products have been reported to be present in the nucleus after infection. The two gene products are the newly synthesized 47 nucleotide leader RNA and a pre-existing component of infecting virions, a ~30 kDa protein called the matrix protein (M protein). Since transcription, but not protein synthesis, is required for inhibition of pre-snRNA maturation, our first attempts were directed at answering the question of whether the leader RNA was responsible for this inhibition. Our inability to reproduce the inhibition by VSV leader RNA led us to question the role of M protein. This protein, present in about 1800 copies per virion, may be released from virions only upon transcription of the leader RNA, at which point it would e free to migrate into the nucleus.

BRIEF SUMMARY OF THE INVENTION

We show below in Example A that the matrix protein M protein) of vesicular stomatitis virus is a very efficient inhibitor of nucleo-cytoplasmic transport. Synthesis of the ca. 30 kDa protein in X. laevis oocytes greatly reduces both RNA and protein import into nuclei and RNA export, with the notable exception of tRNAs and certain mRNAs. Processing of messenger and transfer RNA precursors within the nucleus appears not to be affected by the M protein, but processing of ribosomal RNA is greatly reduced, perhaps secondary to a reduction in the intranuclear pool of ribosomal proteins. Oocytes contain a protein that cross-reacts with monoclonal antibody directed against M protein, raising the possibility that normal cells contain a homologous protein that modulates nucleo-cytoplasmic transport. The great specificity with which M protein can affect transport indicates that it will be a very useful reagent in the analysis and control of transport between the nucleus and cytoplasm.

In Example B we describe a selected class of RNAs that can be exported in the presence of M protein. By analyzing the sequences of these RNAs, we can describe a class of nuclear export elements (NEEs) that are sufficient to target an RNA for export from the nucleus to the cytoplasm.

Therefore, the present invention is a method of inhibiting the transport of nucleic acids and proteins between the nucleus and cytoplasm of a cell (from the nucleus to the cytoplasm and from the cytoplasm to the nucleus). The method comprises the step of exposing a cell to a sufficient quantity of vesicular stomatitis virus (VSV) M protein such that the transport of RNA and proteins through the nuclear envelope of the cell is impeded.

The present invention is also a method of inhibiting transport of nucleic acids and proteins between the nucleus and cytoplasm of a cancer cell or the cells of pathogenic eukaryotes. This method comprises the step of exposing a target cell to a sufficient quantity of vesicular stomatitis virus M protein such that the transport of RNA and proteins through the nuclear envelope of the cell is impeded.

The present invention is also a method of inhibiting transport of nucleic acids and proteins between the nucleus and cytoplasm of a cell using a derivative of the M protein. This method involves examining the vesicular stomatitis virus M protein to determine smaller fragments that retain the ability to inhibit nucleo-cytoplasmic transport. One then exposes a cell to a sufficient quantity of the fragment such that transport of nucleic acids and proteins across the nuclear envelope of the cell is impeded.

The present invention is also a method of inhibiting transport of nucleic acids and proteins between the nucleus and cytoplasm of a cell using a homologue of the vesicular stomatitis virus M protein. This homologue is obtained by examining the protein population of a eukaryotic organism to obtain a protein with sequence similarities to the VSV M protein. One then exposes a cell to a sufficient quantity of the homologue such that transport of RNA and proteins across the nuclear envelope of the cell is impeded. As described above, one may wish to determine smaller fragments of the homologue protein which still retain the ability to inhibit nucleo-cytoplasmic transport. These smaller fragments may be useful in therapeutic applications.

The present invention is also a method to use the cellular homologue of M protein to screen compounds, such as antibiotics, that could alter the activity of such proteins and to use such compounds as a means of inhibiting nucleo-cytoplasmic transport in targeted cells.

The present invention is also a method to identify cellular factors that interact with the M protein or its cellular homologue and to use such factors as targets to screen compounds, such as antibiotics, that could alter the activity of the factor and to use such compounds as a means of inhibiting nucleo-cytoplasmic transport in targeted cells.

The present invention is also a method of inhibiting the export of nucleic acids, particularly RNA, from the nucleus to the cytoplasm of a cell comprising the step of exposing a cell to a sufficient quantity of vesicular stomatitis virus M protein or M protein homologue such hat the import of RNA through the nuclear envelope of he cell is impeded.

The present invention is also a method of inhibiting the import of proteins and RNA-protein complexes from the cytoplasm to the nucleus of a cell comprising the step of exposing a cell to a sufficient quantity of vesicular stomatitis virus or M protein homologue such that the import of proteins through the nuclear envelope of the cell is impeded.

The present invention is also a method of selecting nuclear export elements comprising exposing a cell to M protein or M protein homologue in a sufficient quantity such that nuclear export of RNA molecules is impeded and obtaining and analyzing RNA molecules that are exported in the presence of M protein.

The present invention is also a chimeric RNA comprising nuclear export element (NEE) sequences sufficient to target an RNA molecule for export from the nucleus to the cytoplasm. Preferably, these sequences are selected from the group consisting of SEQ ID NOS: 3–8.

The present invention is also a method of targeting RNA to the cytoplasm. The method begins with the step of creating a chimeric RNA comprising an NEE sequence sufficient to target the RNA for export from the nucleus to the cytoplasm and a target RNA sequence. The RNA molecule is then introduced into a target cell. (Preferably, the RNA molecule is expressed from a DNA construct in the nucleus of the target cell.) The NEE of the chimeric RNA will direct export of the RNA to the cytoplasm of the cell.

The present invention is also a method of inhibiting macromolecular transport within the nucleus of a cell comprising the step of exposing a cell to a sufficient quantity of vesicular stomatitis virus M protein or M protein homologue such that the transport of RNA and proteins within the nucleus of the cell is impeded.

We envision that all of the above methods may be performed both in vitro and in vivo and may be performed with a variety of eukaryotic cell types.

It is an advantage of the present invention that nucleo-cytoplasmic transport of nucleic acids and proteins may be inhibited in an efficient and reproducible manner.

It is another advantage of the present invention that cells react in a differential matter to M protein nucleo-cytoplasmic transport inhibition.

It is another advantage of the present invention that RNAs are created that are capable of export into the cytoplasm even in the presence of M protein.

Other features, advantages and objects will become apparent to one of skill in the art after examination of the specification and claims.

BRIEF DESCRIPTION OF THE SEVERAL VIEWS OF THE DRAWINGS

FIGS. 1A and B diagram the results of experiments designed to identify selection of RNAs containing nuclear export elements (NEEs). FIG. 1A shows enrichment of injected RNA pools for RNAs containing NEEs. FIG. 1B shows selected regions from the sequences of ET-RNAs (Exported RNAs) after 18 rounds of selection. The dashes in SEQ ID NOs:3–8 indicate continued sequences obtained from the carrier (SEQ ID NOs:9 and 10). The dashes in the carrier indicate sequences from the combinatorial library. "Δ" indicates deleted sequences relative to the starting material.

DETAILED DESCRIPTION OF THE INVENTION

A. INHIBITION OF NUCLEAR/CYTOPLASMIC TRANSPORT

The experiments disclosed below in the Examples demonstrate that the VSV M protein is able to block maturation of pre-snRNAs. Moreover, we show that this inhibition results from the ability of M protein to inhibit the Ran/RCC1/GTP-dependent transport of most proteins and RNAs though the nuclear envelope. As with RCC1 inactivation, this virion protein leaves unaffected the system responsible for export of tRNAs. The Examples below also disclose use of M protein to isolate RNAs that may be exported to the cytoplasm even in the presence of M protein. From the sequence of the RNAs, we are able to construct chimeric RNAs so that the RNA molecules may be therapeutically delivered to the cytoplasm.

The present invention is a method of inhibiting transport of nucleic acids and proteins between the nucleus and cytoplasm of a cell. By "inhibiting transport" we mean to include both the inhibition of the export of RNA from the nucleus to the cytoplasm and the import of proteins and protein-RNA complexes from the cytoplasm to the nucleus. This method comprises the step of exposing a cell to a sufficient quantity of vesicular stomatitis virus M protein such that transport of RNA or proteins through the nuclear envelope of the cell is impeded. By "impeded", we mean that the transport of any particular RNA molecule or protein molecule is less than 50%, preferably less than 5%, than that of a control system.

This exposure may be either in vitro or in vivo.

We envision that a variety of cell types will be useful for the present invention. Particularly, cancer cells, which are rapidly dividing, are a preferred cell type and may be particularly sensitive to small amounts of M protein or its derivatives because these cells must carry out nucleo-cytoplasmic transport at high levels. Therefore, one advantageous use of the present invention would be to treat a cancer-stricken organisms with M protein or derivative of M protein or compounds that affect the activity of the cellular homologue of M protein or its interacting factors in a manner that does not adversely affect normally growing cells but does inhibit nucleo-cytoplasmic transport of RNA and proteins in the rapidly growing cancer cells.

Other eukaryotic cells are suitable for the present invention. Particularly, parasitic eukaryotes such as yeast, protozoa or invertebrate metazoans are particularly preferred. Therefore, another advantageous use of the present invention would be to treat a pathogen-infected organism with M protein or derivative of M protein or compounds that affect the activity of the cellular homologue of M protein or its interacting factors in a manner that does not adversely affect normally growing cells but does inhibit nucleo-cytoplasmic transport of RNA and proteins in the parasitic cells.

Our data showing only partial inhibition of growth of S. cerevisiae by M protein shows that this eukaryote uses a related but non-identical protein target in its nucleo-cytoplasmic transport.

We envision that one may wish to examine the M protein to determine a smaller fragment that still possesses the ability to inhibit nucleo-cytoplasmic transport. Because this protein also functions in the assembly of virion particles, it is likely that much of its structure is not needed for the inhibition of transport. One of skill in the art of molecular biology would know how to create the necessary mutations to determine which regions of the protein are necessary for inhibition of nucleo-cytoplasmic transport and would know which regions to delete, thereby reducing the size of the M protein without reducing its ability to impede transport.

Once small derivatives of the protein have been made, one would wish to test various cell types with these derivatives. It is likely that different cells contain different homologous proteins that will react differently to the derivatives. Once one finds differentiation—for example, if a parasitic cell reacts more favorably to a particular derivative or inhibitor than a mammalian cell—one would wish to use this advantageous fragment or inhibitor in a therapeutic manner. One could treat a parasite-infected patient with a therapeutic dose of the M protein derivatives or inhibitors. The dose would inhibit nucleo-cytoplasmic transport in the parasite but not harm the patient.

The experiments below indicate that M protein may be produced in a variety of manners. In one set of experiments, we used oocytes of the frog Xenopus laevis that had been preincubated with M protein mRNA. Therefore, the M protein was produced intracellularly by translation of the M protein from RNA. We describe below a method of obtaining M protein mRNA.

We envision that similar results will be obtained using a purified protein preparation. Purified M protein may be obtained from virions of VSV or from cells containing genes encoding VSV M protein or the mRNA for M protein. For example, the cells can be bacteria or yeast cells that have been transformed by plasmid DNA containing the gene or they can be Xenopus laevis oocytes into which the mRNA has been injected. Purification can be facilitated by addition to the gene of a region encoding a short series of amino acids such as several histidine residues so that the protein may be isolated by affinity chromatography. In our lab, we have successfully injected recombinant protein into oocytes and found that this system works well to inhibit nucleic acid and protein transport.

To construct histidine-tagged M protein, wild-type matrix protein (Orsay strain) could be used as a template for PCR with primers that generate an NdeI restriction site at the start of the coding region and on AvaI site at the end. The PCR product could be cleaved with NdeI and AvaI and cloned in frame with the coding region for 6 Histidines into pET216 obtained from Novagen, Inc. and cleaved with the same enzymes. The final clone may be verified by dideoxy sequencing.

If one wishes to expose a cell in vivo to M protein, one would typically create M protein mRNA-infected cells through a variety of methods known to one of skill in the art or administer the M protein directly. For example, Black and Lyles (J. Virol. 66:4058, 1992) disclose the M protein mRNA. M protein and M protein mRNA are also disclosed in Rose and Gallione, J. Virol. 39:519, 1981. (Both the Black and Lyles and Rose and Gallione articles are hereby incorporated by reference.) This direct administration may be through the methods of microinjection, attached to particles, by liposome fusion or in virions or virus pseudotypes. Alternatively, one might transfect a DNA sequence encoding the M protein or an appropriate M protein derivative into cells, preferably using a controllable expression system such as that of the chloramphenicol resistance gene or a metal-inducible promoter.

Inhibition of protein or RNA transport may be measured by methods known to one of skill in the art or by methods disclosed below in the Examples. The Examples below disclose preferred methods.

B. USE OF NUCLEAR EXPORT ELEMENTS DESIGNED TO PERMIT RNA TO BE EXPORTED

The present invention is also a method of selecting nuclear export elements (NEEs), comprising the steps of exposing a cell to a sufficient quantity of M protein or M protein homologue such that export of RNA from the nucleus to the cytoplasm is impeded and selecting an RNA molecule or molecules that are exported in the presence of M protein. One would analyze the selected RNA in order to isolate the NEE sequences. Preferably, suspected NEE sequences would be attached to RNA molecules that are not efficiently exported to the cytoplasm. The transport of these chimeric RNAs could be examined and would indicate whether the selected sequence could function as an NEE.

In the examples below, using M protein as an inhibitor of Ran/RCC1 dependent nucleo-cytoplasmic transport in X. lacevis oocytes, we selected RNAs that are capable of being exported by an alternative pathway. Three "winner" selected sequences predominated among the selected RNAs (see FIG. 1; SEQ ID NOs:3, 4 and 5). Almost half of the clones, represented by clone ET-202 (comprising SEQ ID NO:3), had the same sequence; two other clones (ET-208 [comprising SEQ ID NO:4] and ET-201 [comprising SEQ ID NO:5]) each accounted for about a quarter of the total. FIG. 1B discloses the selected sequences with enough of the flanking sequences for orientation. SEQ ID NOs:9 and 10 are the sequence of the original carrier molecule (see FIG. 1B). The entire starting material sequence is disclosed in Grimm, et al., EMBO J. 16:763, 1997, which is hereby incorporated by reference.

Preferably, a chimeric RNA of the present invention comprises SEQ ID NOs:3, 4, 5, 6, 7 or 8. Most preferably, the chimeric RNA of the present invention comprises SEQ ID NOs:3, 4 or 5. One of skill in the art knows that minor sequence changes, such as deletions, mutations and additions can be functionally insignificant. By "SEQ ID NOs:3–8," we mean to cover similar sequences with functionally identical changes. The Examples below disclose preferred methods to determine whether two NEEs are functionally identical.

In another embodiment of the present invention, the chimeric RNA comprises residues 14–33 of SEQ ID NO:3, residues 10–29 of SEQ ID NO:4, residues 10–29 of SEQ ID NO:5, residues 14–33 of SEQ ID NO:6, residues 11–30 of SEQ ID NO:7, or residues 10–28 of SEQ ID NO:8.

To construct the chimeric RNA of the present invention, one would use methods known to one of skill in the art to attach an appropriate nuclear export signal, such as that represented by ET-202, to an RNA of interest. Most typically, this would be done by constructing a chimeric DNA molecule and obtaining the RNA by transcription of the DNA. The sequences of SEQ ID NOs:3–8 may be most easily obtained by chemical nucleic acid synthesis methods.

Most typically, the RNA of interest or "target" RNA is an RNA that otherwise lacks NEE signals and is an RNA that is desirable to export to the cytoplasm.

A typical target RNA is not natively attached to nuclear export elements. However, a suitable target RNA of the present invention may be natively attached to an export signal that performs inefficiently or at a minimal level. By specifying RNAs that are not exported to the nucleus, we mean to include RNAs that are exported at an insufficient level.

One would then create a chimeric molecule by attaching the NEE sequences to the target RNA sequence by methods known to one of skill in the art. The NEE may be located 5' or 3' to the target sequence.

One would not need the entire sequence of the N20 region of ET-202, ET-208 or ET-201, however. One of skill in the art would know that truncation of these sequences would produce a smaller deletion fragment that would also be appropriate. A shortened version of SEQ ID NOs:3–8 is an appropriate NEE of the present invention if it impedes at least 50% of the transport of nucleic acid or protein between the nucleus and cytoplasm.

Examples of RNAs that might be therapeutically targeted to the cytoplasm are antisense molecules, ribozymes and mRNA molecules that are naturally inefficiently transported. (See Westaway, et al., *Nucl. Acids Res.* 23 [suppl.]:194, 1995.)

The present invention is also a method of using these chimeric RNAs in therapy, either at an in vivo or in vitro level.

EXAMPLES

A. INHIBITION OF RAN GTPASE-DEPENDENT NUCLEAR TRANSPORT BY THE MATRIX PROTEIN OF VESICULAR STOMATITIS VIRUS.

1. Materials and Methods a. In General

Clones for various snRNAs and tRNAs and mRNAs are described elsewhere by us and others (M.P. Terns and J. E. Dahlberg, *Science* 264:959, 1994); J. Hamm and I. W. Mattaj, *Cell* 63:109, 1990); A. Krol, et al., *EMBO J.* 4:1529 (1985); I. W. Mattaj, *Cell* 46:905 (1986); F. Muller and S. G. Clarkson, *Cell* 19:345 (1980). pSV-OM was constructed by inserting HindIII fragment carrying full length cDNA clone of VSV Orsay strain matrix protein into the HindIII site of pSV2.Neo vector (B. L. Black, et al., *J. Virol.* 67:4814, 1993). This pSV-OM clone was obtained from D. S. Lyles (Bowman Gray University, North Carolina).

pCUG1 was constructed by inserting a 690 bp GAL1/10 promoter fragment from pBM272 (GeneBank access number U03497) into the polylinker of pRS316 (R. S. Sikorski and J. D. Hieter, *Genetics* 122:19 (1989) using the EcoRI and HindIII sites. pCUG-OM is a derivative of pCUG1 carrying matrix protein gene under the control of the GAL1 promoter. pCUG-OM was constructed by inserting the HindIII fragment carrying the same matrix protein cDNA as above into the multicloning site of pCUG1 using HindIII site. pEUG-OM construct is the same as PCUG-OM, except that a 2 micron origin is substituted for CEN origin. pCUG1 and pEUG1 were obtained from P. A. James (University of Wisconsin, Wisconsin). pSP64-OM-polyA is constructed by inserting the same cDNA clone as above into-HindIII site of pSP64-polyA vector (Promega) under the control of SP6 promoter.

Baby hamster kidney (BHK) cell were grown and RNA was extracted as described (Y. Cheng, et al., *Science* 267:1807, 1995). Transfection of pSV2-OM construct into BHK cell was done by LipofectAmine reagent following the protocol suggested by the manufacturer (Gibco). Immunoprecipitation was performed as described (E. Harlow and D. Lane, *Antibody a Laboratory Manual*, 1988) using anti-M monoclonal antibody 23H12 (L. Lefrancois and D. S. Lyles, *Virology* 121:157 (1982). Monoclonal antibody 23H12 was obtained from D. S. Lyles.

For making mRNA for Xenopus oocyte injection, the template DNA pSP64-OM-poly A was lineralized with EcoRI digestion (B. L. Black, et al., supra, 1993). In vitro transcription was done as described (D. A. Melton, et al., *Nucleic Acids Res.* 12:7035 (1984) using SP6 RNA polymerase from Promega. Injection and manual dissection of oocytes were performed as described (E. Lund and J. E. Dahlberg, *EMBO J.* 8:287 (1989).

Synthetic glucose medium is 2% glucose, 0.67% Bacto yeast nitrogen base w/o amino acids (Difco), which was supplemented with required amino acids as described (F. Sherman, et al., *Laboratory Course Manual for Methods in Yeast Genetics* (Cold Spring Harbor Lab. Press). Synthetic galactose medium is the same as above, except that 2% galactose was substituted for glucose. Yeast strain PJ43-2B is Matα ade2-1 canl-100 GAL2+ his3-11,15 leu2-3,112 lys2-d2 trp1-1 ura3-1. pCUG-OM and pEUG-OM were transformed to PJ43-2B by the method of Scheistl and Geitz (R. H. Schiestl and R. D. Gietz, *Curr. Genet.* 16:339 (1989). The colonies were screened on SC-ura plate.

b. Protein Purification Protocol

Preparation of Culture

1. Grow 5 ml overnight culture of *E. coli* BL21 (DE3) pLys5 containing pET21bT.OMHis6 (L. Lefrancois and D. S. Lyles, supra (1982).

2. Inoculate 500 ml of LBroth (Gibco) with 100 micrograms/ml Amp with 1 ml of the overnight.

3. Grow to an $OD_{600}$ around 0.6 and then add IPTG to 1.1 mM final concentration.

4. Allow the culture to grow another 3 hours. So far this has been done at 37 degrees, but a lower temperature may prove more useful.

5. Place the culture in an ice water bath for 5 minutes.

6. To harvest the cells, spin at 5000×g for 5 minutes at 4 degrees. Divide the sample in two for the centrifugation. So far only 250 ml culture has been used on the column.

7. Remove the supernatant and resuspend the culture (250 ml worth) in 8 ml of Novagen's 1XBinding buffer containing 0.2% Triton X-100.

8. Lyse the cells with a french press. Sonication has not worked well. With 0.2% Triton the french press also not that efficient so may have to pass it through three or four times.

9. Transfer sample to five eppendorf tubes and spin 10 minutes at 14000 rpm at 4 degrees in the cold centrifuge to remove remaining insoluble material.

10. The sample is then filtered through a 0.45 micron syringe filter before loading onto the column. At least 20 microliters of sample are saved for analysis later.

Column Preparation

1. Rinse nickel affinity column (Novagen, Inc.) with 3 volumes of water.

2. Charge column with 5 volumes of Novagen's 1X Charge Buffer.

3. Equilibrate column with 3 volumes of Novagen's 1X Binding Buffer with 0.2% Triton X-100.

Column Chromatography

1. Load extract with syringe to top of column. The column is run at 4 degrees.

2. Rinse with 10 volumes Novagen's 1X Binding buffer with 0.2% Triton.

3. Wash column with 6 volumes Novagen's 1X Wash Buffer with 0.2% Triton.

4. Elute with 6 volumes of elution buffer. 200 microliter fractions are taken until the 15th and then 500 microliter samples are taken. Matrix protein usually elutes by the 11th fraction. The elution buffer used is 20 mM Hepes pH 7.5, 100 mM NaCl, 5% glycerol, 0.2% Triton X-100, 500 mM Imidazole.

Post Column Treatment

Good results have been obtained by first dialyzing into the elution buffer plus 100 mM Imidazole and 0.1% Triton for two hours and then into the elution buffer without Imidazole and with only 0.01% Triton for two hours. Dialysis buffer is changed two more times into this final buffer. The final buffer did not have DTT or 2-mercaptoethanol.

2. Results a. VSV M protein as an inhibitor of pre-snRNA maturation

For several years it has been known that maturation of pre-snRNAs is inhibited soon after infection of cells by VSV, but the mechanism of inhibition was not understood. We asked if that could occur by VSV promoted inhibition of export of pre-snRNAs since these molecules undergo maturation only after being transported to the nucleus. We first tested several cloned VSV genes, to determine which gene product might be sufficient to cause the inhibition of snRNA maturation in tissue culture cells.

Baby hamster kidney cells in culture were cotransfected with DNAs encoding a maxi-U1 snRNA gene and several versions of the M protein of VSV. The maxi-U1 gene contained the human U1 snRNA gene Bi-33, which has a duplication of 33 nucleotides at its 5'-end (J. E. Dahlberg and E. T. Schenborn, *Nucleic Acid Res.* 16:5827 (1988). Versions of the M protein gene included the coding region in the sense and antisense orientations, as well as the empty vector alone, pSV2 neoDNA. RNAse protection assays of newly synthesized maxi-U1 RNA demonstrated that the RNA accumulated both in the presence and absence of functional M protein gene. However, when cells could make a functional version of M protein, the fraction of maxi-U1 RNA that was present in its precursor form rose from about 2.5% to about 10% of the total. Precipitation of the accumulated RNAs, using antibody directed to $m^7G$ caps showed a significant increase in the relative level of precursor maxi U1RNA in the presence of M protein. The lack of complete inhibition of maturation was expected, as the cells were able to make maxi U1RNA prior to accumulation of an inhibitory level of M protein. We conclude that no VSV gene product other than M protein is needed to inhibit maturation of pre-snRNAs. Moreover, using the criterion of maturation as a measure of export (Y. Cheng, et al., supra, 1995), it is likely that M protein acts through inhibition of nucleo-cytoplasmic export.

b. Expression of VSV M protein in Xenopus oocytes

To test directly if VSV matrix protein (M protein) is responsible for the accumulation of snRNA precursors that is observed in VSV-infected mammalian cells, we asked whether M protein that was previously synthesized in Xenopus oocytes could inhibit maturation of newly synthesized snRNA. To do so, we first investigated whether M protein accumulated in the cytoplasms of Xenopus oocytes into which the mRNA that encoded M protein (M-mRNA) had been injected. As a control for nonspecific effects due to the injection of large amounts of exogenous mRNAs (10–20 ng/oocyte), oocytes were also injected with similar amounts of "antisense" mRNA (i.e. RNA complementary to M protein mRNA). The $m^7G$-capped, polyadenylated mRNA transcripts were synthesized in vitro by transcription with SP6 RNA polymerase, and both coding and antisense RNAs were found to be relatively stable in oocyte cytoplasms (not shown). Accumulation of M protein was detected either directly by labeling of the injected oocytes with $^{35}S$-labeled amino acids (methionine+cysteine) and autoradiographic analyses of the newly made labeled proteins, or indirectly by immunoblotting using monoclonal antibodies specific to VSV matrix protein (L. Lefrancois and D. S. Lyles, supra (1982).

The results of such analyses indicated that authentic M protein was made, as judged both by its electrophoretic mobility and by binding to the anti-M protein antibodies. In addition, we found that M protein continued to accumulate for at least up to 48 hours after RNA injection. As expected, injection of "antisense" mRNA resulted in no detectable synthesis of novel protein products.

Analyses of proteins made with or without injection of M protein mRNA into oocyte cytoplasms revealed a protein with an approximate molecular weight of about 50–60 kDa that consistently cross-reacted with monoclonal antibody directed against M protein. Such a protein might represent the cellular equivalent of the VSV M protein.

c. Activity of M protein in Xenopus Oocytes

We then asked whether the presence of M protein affected snRNA maturation. For these experiments, oocytes were injected with either M-mRNA or control "antisense" mRNA and allowed to incubate for 24 hours to express M protein (see above). After this preincubation, all oocytes were injected in the nucleus with a mixture of DNA templates encoding Xenopus U1, U2 and U3 snRNAs; two hours later, the oocytes received a third injection in the cytoplasm with $^{32}P$-GTP, to label the newly synthesized RNAs. After 20 hours of labeling, the expression and intracellular distributions of the labeled snRNAs were determined by manual dissection of the oocytes and analyses of the isolated nuclear and cytoplasmic RNAs by polyacrylamide gel electrophoresis. Strikingly, the oocytes expressing M protein showed an approximately a 10-fold reduction in the cytoplasmic levels of both U1 and U2 snRNAs, relative to those of the control oocytes. These results indicated that export of newly-made snRNAs was inhibited in the presence of M protein. In contrast, the total amounts of accumulated U1 and U2 RNAs (precursor plus mature RNA) were decreased by only 2–3 fold, demonstrating that transcription of the injected snRNA genes was relatively unaffected by M protein. Consistent with this, the accumulation of U3 snRNA, which normally is retained in the nucleus, showed no significant difference between the two sets of oocytes.

To confirm that blockage of export was responsible for the lack of cytoplasmic accumulation of U1 and U2 snRNAs, nuclear RNAs from both the control and M protein containing oocytes were immunoprecipitated with antibodies directed against the $m^7G$-cap structure specific to the immature precursors of snRNAs (pre-snRNAs) (Y. Cheng, et al., supra, 1995). Normally, the $m^7G$-capped pre-snRNAs are exported to the cytoplasm very shortly after synthesis. In the cytoplasm, the precursors immediately become associated with the common Sm-proteins, which, in turn, leads to rapid modification of the cap-structure to the $m^{2,2,7}G$ hypermethylated form. The mature snRNPs are then imported back into the nucleus (I. W. Mattaj, supra (1986). Thus, the level of $m^7G$-capped pre-snRNAs usually accounts for less than 5% of the total snRNA present in the nucleus, as was observed here for the control oocytes.

In contrast, we found that 80% (U2) or close to 95% (U1) of the nuclear snRNAs in oocytes containing M protein were precipitable by the anti-$m^7G$ antibodies, indicating that cap-modification, and hence export from the nucleus, had not occurred. In addition, these immunoprecipitation analyses clearly demonstrated that cap-hypermethylation of U3 RNA, which unlike that of U1 and U2 snRNA is nuclear event (M. P. Terns and J. E. Dahlberg, supra, 1994); M. P. Terns, et al., supra, 1995). was not affected by the presence of M protein.

Thus, we conclude that the presence of M protein profoundly impairs the export of snRNA precursors made in Xenopus oocytes. We propose that a similar block of RNA export is responsible for the abrupt cessation of snRNA maturation that occurs very soon after VSV infection in mammalian cells.

Because both snRNAs and mRNAs contain an $m^7G$-cap structure, which serves as a signal for RNA export (M. P. Terns, et al., *Genes Dev.* 7:1898, 1993); A. Jarmolowski, et al., *J. Cell Biol.* 124:627, 1994), it was important to determine whether the inhibition of RNA export induced by M protein was limited to pre-snRNAs or also affected mRNAs. To monitor the export of mRNA, we utilized a derivative of adenovirus major late (AdML) pre-mRNA, which is very efficiently spliced in oocytes (J. Hamm and I. W. Mattaj, supra, 1990) and which generates a short mRNA that is exported with similar kinetics as pre-U1 RNA. As controls for export and the accuracy of nuclear injection and dissection, the pre-mRNA was injected together with $U1_{sm^-}$ RNA, which lacks the Sm binding site required for import back into the nucleus (J. Hamm and I. W. Mattaj, supra, 1990), and U6 snRNA, which is retained in the nucleus (M. P. Terns, et al., supra, 1993); J. Hamm and I. A. Mattaj *EMBO J.* 8:4179 (1989).

All of the injected RNAs were $^{32}P$-labeled and were synthesized in vitro by transcription with SP6 polymerase. Again, we used oocytes that had been preinjected with M-mRNA or "antisense" mRNA (see above). The mixture of $^{32}P$-labeled RNAs was injected into the oocyte nuclei and both splicing and export were followed as a function of time.

When assayed 1 hour after RNA injection, export of the spliced mRNA, like that of $U1_{SM}$-RNA, was completely blocked in M protein treated oocytes, whereas close to 50% of both RNAs had been exported in the control oocytes. However, at later times (4 hours post injection) a small but significant amount of mRNA was observed in the cytoplasm. This was in contrast to the persistent blockage of snRNA export. We also note, that intranuclear functions like splicing of the injected pre-mRNA and nuclear retention of U6 snRNA were unaffected by the presence of M protein. Thus, these results indicate that both pathways for export of $m^7G$-capped RNAs are sensitive to inhibition by M protein, albeit to slightly different extents.

Although several studies have shown that RNA polymerase III transcripts are exported via different pathways than $m^7G$ capped RNAs (A. Jarmolowski, et al., supra, 1994), recent findings have indicated that the export machinery of 5S ribosomal RNA and U1 RNA have one (or more) component(s) in common (U. Fischer, et al., *Cell* 82:475, 1995). In contrast, export of tRNA utilizes a pathway that clearly differs from that used by all other RNAs (A. Jarmolowski, et al., supra, 1994). To establish whether M protein is an effective inhibitor of the export of these two types of RNA polIII transcripts, we compared the intracellular distributions of newly made 5S rRNA (transcribed from the endogenous, highly reiterated oocyte 5S rRNA genes) and $tRNA^{Tyr}$ (transcribed from injected Xenopus tRNA genes) in the presence and absence of M protein. The export of 5S rRNA clearly resembled that of U1 or U2 snRNAs in its susceptibility to inhibition by M protein. In contrast, both export and intranuclear processing of $RNA^{Tyr}$ occurred with identical kinetics in the two sets of oocytes. Similar results were obtained when the export of another tRNA, Xenopus $tRNA^{Asn}$, which is not subject to splicing, was assayed. These results therefore underscore the fundamental, but still poorly understood, difference between export of tRNA and that of most other RNAs.

To determine if export of the large 18S and 28S ribosomal RNAs, which utilizes yet a different pathway, was equally sensitive to M protein, we examined the metabolism of endogenous oocyte rRNAs that were synthesized between 20 and 40 hours after injection of M-mRNA. Normally, processing of the primary 45S rRNA transcript occurs in a large ribonucleoprotein complex that is localized in the nucleolus (B. A. Peculis and J. A. Steitz, *Cell* 73:1233, 1993). Unlike other intranuclear processing events such as mRNA and tRNA splicing (see above), under these conditions, formation of the mature forms of rRNAs was sharply curtailed, as shown by the absence of 18S and 28S rRNAs in M-treated oocytes. In some batches of oocytes, low levels of 18S and 28S RNAs were detectable, but these RNAs remained exclusively in the nucleus. Thus these results show that the presence of M protein affects not only the maturation, but also the export of ribosomes.

Because both maturation and export of rRNA are dependent on the import of ribosomal proteins into the nucleus (N. Bataille, et al., *J. Cell Biol.* 111:1571, 1990), we tested directly if nuclear import also was affected by M protein. In this case, $^{35}S$-labeled Xenopus karyophilic proteins were used as the import substrate; 0.25 oocyte equivalents of such total nuclear soluble proteins were injected into the cytoplasms of oocytes that had been pre-injected with M-mRNA or "antisense" mRNA as above, or which had been injected with the inhibitor of nucleo-cytoplasmic transport wheat germ agglutinin (WGA) 1–2 hours earlier. Following overnight incubation to allow for high levels of protein import, the intracellular distributions of two prominently labeled Xenopus nuclear proteins, N1/N2 (Dabauvalle, et al., *Exp. Cell Res.* 174:291 (1996), were determined by SDS polyacrylamide gel electrophoresis of the isolated nuclear and cytoplasmic extracts. Under these conditions, we found that M protein was equally effective as an inhibitor of protein import as was treatment with WGA. Compared to the level of N1/N2 import in the control oocytes, we estimate that protein import was reduced by close to 90% in the presence of M protein.

In parallel experiments, we also monitored the effects of M protein on the import of two types of RNAs, U5 and U6 snRNA, which utilize the import pathways specific for snRNPs and NLS-containing proteins, respectively (U. Fischer, et al., *J. Cell Biol.* 113:705, 1991). In agreement with the strong inhibition of protein import, import of U6 RNA was undetectable. Surprisingly, we found that M protein was an equally potent inhibitor of the import of U5 snRNA. Previous studies have shown that import of U5 snRNP is quite insensitive to a variety of inhibitors of NPC function, such as WGA and anti-nucleoporin antibodies (U. Fischer, et al., supra, 1991). Thus these results make M protein the first "universal" inhibitor of import from the cytoplasms into the nucleus.

In conclusion, we propose that M protein interferes with a central component of the transport machinery, that utilizes the RCC1/Ran-GTPase system (Y. Cheng, et al., supra, 1995), which we and others have recently shown to required for the nucleocytoplasmic trafficking via most, albeit not all, transport pathways.

d. Expression of VSV M protein in Yeast Cells

We questioned if the nucleo-cytoplasmic transport machinery of *S. cerevisiae* utilized components that would respond to inhibition by VSV M protein. To answer this question we cloned the gene using the yeast GalI promoter, which can be controlled by addition of sugars to the medium. Use of a controllable promoter allowed us to transfect yeast with a gene whose product would be likely to inhibit growth or kill the cells. In the absence of galactose and the presence of glucose, no difference in growth rate or colony size was observed between cells containing either the sense or antisense versions of the M protein gene. However, upon induction of the promoters by removal of glucose and addition of galactose a significant decrease in growth rate was observed for cells containing a functional M protein gene.

These results show that M protein also affects the viability of lower eukaryotes. While we have not demonstrated that the effect is on nucleo-cytoplasmic transport in these cells, such a mechanism seems likely. Many of the components that participate in this process are analogous in higher and lower eukaryotes, but several of these factors differ sufficiently from each other that they cannot function in the other type of cell. Thus, the factors in yeast that might interact with M protein may differ in structure sufficiently to give only a partial inhibition of transport and growth.

3. Discussion

We have shown here that a protein encoded by the matrix protein gene of VSV is able to inhibit transport of proteins and RNAs between the nucleus and cytoplasm, in a selective manner. While most of the experiments were performed using in vitro synthesized mRNA for the M protein, it is very likely that the same results will be obtained using the purified protein.

The selectivity of the inhibition of transport by M protein is very striking. The protein inhibits export from the nucleus of all RNAs except tRNAs, and it inhibits the import of both proteins and ribonucleoproteins (RNPs). However, M protein seems not to affect intranuclear processing events such as the splicing of mRNA-precursors or tRNA-precursors or the hypermethylation of the 5' cap of U3 small nucleolar RNA.

The pattern of inhibition of transport observed here closely resembles the consequences of inactivation of the nuclear GTP:GDP exchange factor RCC1. Thus, the same essential pathway of events may be inhibited by loss of RCC1 or by the presence of M protein. It is unclear if the same step in this pathway is affected by the two treatments.

The discovery that M protein specifically inhibits nucleo-cytoplasmic transport opens new opportunities to modulate Ran/RCC1-dependent transport without directly affecting intranuclear events such as splicing. This will be useful to those who want to analyze or manipulate transport in whole cells or cell preparations, without directly perturbing other nuclear functions. It can be done either by microinjection of the M protein itself or its mRNA into cells, allowing for selective inhibition of transport in intact, living cells. Alternatively, the gene for this protein might be transfected into cells, using a controllable expression system such as that of the tetracycline resistance gene or a metal-inducible promoter.

M protein promises to be a useful tool for investigators studying the mechanism of nucleo-cytoplasmic transport, since this protein must interact with, and inhibit, one or more factors that are essential to this process. Identification of these interacting factors will reveal cellular gene products that function in these events and will help establish the overall pathways of export and import.

By stopping most export/import events, use of the M protein will allow reduction of the background that could obscure analysis of other forms of transport. For example, we have shown (Y. Cheng, et al., supra, 1995) that export of tRNA occurs by an pathway independent of RCC1 function, indicating that this class of RNA uses its own export pathway. The availability of M protein inhibition of the Ran/RCC1-dependent pathway allows the tRNA specific mechanism to be studied in detail.

Because this protein also functions in the assembly of virion particles, it is likely that much of its structure is not needed for the inhibition of transport. Thus, an understanding of this latter activity may allow for development of smaller agents that can be introduced into cells. Ultimately, this knowledge could serve as the basis of rational drug design in the development of specific inhibitors of nucleo-cytoplasmic transport. Rapidly dividing cancer cells might be particularly sensitive to such small derivatives of M protein since these cells must carry out nucleocytoplasmic transport at high levels. Similarly, it may be possible to develop derivatives that would inhibit this transport in specific cell types, for example in parasitic eukaryotes such as yeasts, worms or malaria; our data showing only partial inhibition of growth of S. cerevisiae by M protein shows that this lower eukaryote uses a related but nonidentical protein target in its nucleocytoplasmic transport. Thus, an M protein homologue or interacting factor might be differentially sensitive to antibiotics.

Using monoclonal antibodies to M protein we have detected a cross-reacting protein in normal X. laevis oocytes. That raises the possibility that normal cells have a similar protein that might modulate the extent of nucleo-cytoplasmic transport.

M protein must interact with cellular factors to elicit inhibition of NC transport. Thus, the interacting factors or cellular homologue of M protein are potential targets for treatments that would modify their activity. Such factors can themselves be used as targets in screening for compounds that could alter the activity of the nucleo-cytoplasmic transport system in various types of cells, and ultimately as targets for therapeutic treatment.

The utility of the M protein of VSV and the genetic information that encodes this protein (as DNA or RNA) can be used in both basic and therapeutic applications. In basic science it is a very convenient way to down-regulate the Ran/RCC1-dependent nucleocytoplasmic transport system so that other systems, such as that used for tRNA transport, can be studied more readily. It also will be a convenient way to discover and study additional factors that are used in the Ran/RCC1-dependent pathway and discover new RNA sequences that use another export pathway. Results from studies on the M protein, the cellular equivalent of this protein and the factors with which these proteins interact can serve as the basis for rational design of drugs that would alter these activities in cells associated with various pathologies.

B. NUCLEAR EXPORT AND IMMOBILIZATION OF RNA

1. In general

The correct distribution of RNA and protein molecules between the nucleus and cytoplasm of cells is essential for gene expression. Retention within the nucleus or transport through nuclear pore complexes (NPCs) of the nuclear envelope allow for the sequestration of RNAs in cell compartments appropriate for processing or function. RNAs contain cis-acting regions that determine intracellular localization and efficiency of transport, either by promoting retention or export. We refer to these RNA domains as nuclear retention elements (NREs) or nuclear export elements (NEEs). In all cases investigated to date these domains function by interacting with trans-acting nuclear factors.

Specific retention of RNA has been demonstrated both for small nucleolar RNAs such as U3 and U8 and for spliceosomal U6 small nuclear RNA (M. P. Terns, et al., supra, 1995); W. C. Boelens, et al., RNA 1:273–283, 1995). The abundant nuclear antigen La promotes nuclear retention of several RNAs including hY1 RNA (F.H.M. Simons, et al., *RNA* 2:264–273 (1996)) and NL-15 RNA, a molecule selected for its localization in nuclei (C. Grimm, et al., *EMBO J.* 16:793, 1997). We have proposed that movement of RNAs within the nucleoplasm may be retarded by interaction of RNA-protein complexes (RNPs) with immobile nuclear structures and that the delivery of an RNA to an appropriate intranuclear location may depend on hydrolysis of GTP mediated by GTPase Ran (Y. Cheng, et al., supra, 1995).

Two transacting RNA export factors and their corresponding cis-acting elements (NEEs) in RNAs have been characterized in some detail. The cap binding complex (CBC) recognizes the $m^7G$-cap structure of RNAs transcribed by RNA polymerase II facilitates the efficient export of pre-snRNAs (E. Izuarralde, et al., *Nature* 376:709–712, 1995). The Rev protein from Human Immunodeficiency Virus (HIV) recognizes the Rev Responsive Element (RRE) in HIV pre-mRNAs, allowing unspliced viral pre-mRNA to be exported to the cytoplasm (M.H. Malim, et al., *Nature* 338:254–257 (1989); U. Fischer, et al., supra, 1995). Both of these factors exit the nucleus with the RNA cargo and must subsequently be reimported.

The export of many RNAs is dependent on the GTPase Ran and its associated binding-, exchange- and activation-factors; when this system is inactivated by mutation of one of its components or by the introduction of inhibitors most nucleo-cytoplasmic transport ceases, with only the export of tRNA and stress-related mRNAs continuing. The Ran system also is required for protein import (M. S. Moore and G. Blobel, *Nature* 661–663, 1993), so loss of Ran function may result in nuclear depletion of RNA export factors that shuttle between the nucleus and cytoplasm. The potential coupling of RNA export with protein import makes it difficult to determine if the Ran system is needed for RNA export per se and a direct role of Ran and its associated factors in RNA export remains to be established.

We have shown in Example A that the Matrix (M) protein of vesicular stomatitis virus (VSV) is a very effective inhibitor of Ran-dependent protein import and RNA export. The ability to introduce this inhibitor into Xenopus laevis oocytes gives us the ability to inhibit Ran-dependent transport and we have used it to differentiate between steps in RNA export that may or may not be coupled to protein import. To do that, we selected a class of RNAs that can be exported very efficiently in the presence of M protein. The selected sequences act as export elements in chimeric RNAs that contain RNA sequences that are otherwise exported inefficiently or not at all. Surprisingly, unlike the RNAs containing solely the selected sequences, these chimeric RNAs are very poorly exported in the presence of M protein. This indicates that the natural, non-selected sequences introduce into the chimeras an extra requirement for transport that is detectable only in the presence of M protein. We propose that most RNAs are normally immobilized in the nucleus and that their release, prior to export, is inhibited when nucleo-cytoplasmic transport is impaired by M protein.

2. Materials and Methods

DNA Templates and In Vitro Transcription

DNA templates for in vitro transcription were generated by PCR amplification of RNA coding regions using appropriate primer pairs. Templates used to transcribe U1, U1124, U2, U3, U6 and hY1 RNAs were described previously (M. P. Terns, et al., supra, 1995); M. P. Terns, et al., supra, 1993); F. H. M. Simons, et al., *RNA* 2:264–273 (1996)). The U6Xho DNA template was constructed by amplifying the U6 RNA coding region with a 5' primer containing the T7 promoter and a 3' primer containing an XhoI site adjacent to the U6 coding region. The DNA was cut with XhoI prior to transcription. This DNA also was used to construct the DNA templates for the chimeric U6 RNAs (see below). In vitro transcription, selection and purification of RNAs were done as described elsewhere (C. Grimm, et al., *EMBO J.* 16:793, 1997, incorporated by references as if fully set forth below).

To construct the ET-202 dimer (ET-202/di) template, DNA encoding ET-202 RNA under the control of a T7 promoter was cloned into pGEM4Z (Promega), using a HindIII linker 5' of the T7 promoter and a EcoRI linker 3' of the ET-202 coding sequence. A second ET-202 coding region (flanked by EcoRI linkers) was then inserted into the EcoRI site of this plasmid. The orientation of the insert was verified by PCR amplification using primer pairs sensitive to the sense or antisense orientation of the second ET-202 DNA. The plasmid containing two ET-202 coding regions in sense orientation and an appropriate pair of primers were used to amplify a DNA template containing the T7 promoter and the coding sequence for ET-202/di with the ET-202 3' end.

To construct the chimeric Ad/ET-202 and Ad/aET-202 DNA templates, ET-202 DNA containing ScaI and EcoRV linkers on the 5' and 3' side, respectively, was cloned into the SmaI site of pSP64-Ad1 (M. A. Powers, et al., *J. Cell Biol.* 136:241, 1997) which contains exon one, a shortened form of intron one and 45 nucleotides of exon two of the adeno major late (AdML) coding region (M. M. Konarska and P. A. Sharp, *Cell* 49:763–774). Orientation of the ET-202 insert in individual clones was determined by PCR amplification using primer pairs that were sensitive for sense or antisense orientation of the insert. Plasmids containing ET-202 sequence in sense or antisense orientation were used together with appropriate primer pairs to amplify DNA containing an SP6 promoter and the coding region of the chimeric RNAs. Ad/ET-202 RNA had the precise ET-202 3' end, but Ad/aET-202 RNA had an additional trinucleotide (AGU) at the end of the antisense sequences of ET-202 RNA.

DNA templates for other chimeric RNAs were constructed by ligating DNA of the appropriate RNA coding regions via linker sequences. The ligated products were amplified by PCR using primer pairs selective for the chimeric DNA. The linker sequences separating the two coding regions in the chimeric RNAs were: 5+-CTCGAGTACT-3+(SEQ ID NO:1) (for U2Sm-/ET-202; U1124/ET-202; U1124/ET-208; U6/ET-202; U6/SLX); 5+-GAATTCGATTTAGGTGACACTATA-3+ (SEQ ID NO:2) (for ET-202/U2Sm-; SLX/U2Sm-).

Oocyte Injections and in vivo Selection

Oocytes injections and dissections were done as described (M. P. Terns, et al., supra, 1995); for export in presence of mAb414, RNAs were mixed with 3mM DTT, RNasin and the antibody (at a final concentration of 5 mg/ml) prior to injection. tRNAPhe from yeast (Sigma) was used as unlabeled competitor tRNA.

The structure of the DNA template used to prepare the RNA for the first round of selection and the general scheme for in vivo selection have been described recently (C. Grimm, et al., supra, 1997). To select for RNAs that are exported in presence of the matrix protein of VSV (M protein; rounds 1–12 and 17–18), mRNA for M protein was pre-injected into oocyte cytoplasms (Her, et al., *Science*, in press). 16 to 20 hours later, when the M protein was expressed at levels sufficient to inhibit most nucleocytoplasmic transport, the pool of uncapped RNAs containing the randomized sequence (N=20) was injected into nuclei along with several control RNAs for nuclear retention (e.g. U3 or U6) and export (e.g. U1Sm-). After two hours of incubation at 18° C., oocytes were dissected and RNAs were prepared from both nuclear and cytoplasmic fractions. The exported RNAs (in the cytoplasms) were purified by size selection in a denaturing polyacrylamide gel containing 7M urea and the selected RNAs were amplified by reverse transcription coupled to PCR (RT-PCR). The resulting DNA templates were used to prepare the RNA for the next round of selection. The counter-selection (rounds 13–16) to ensure active transport was done by injecting RNAs into oocytes kept at 0° C. After 20 hours of incubation on ice, the not-exported RNAs (in the nucleus) were isolated and amplified as above. The final RT-PCR products of exported RNAs in presence of M protein (round 18; ET-RNAs, see FIG. 1) were cloned and sequenced as described (C. Grimm, et al., supra, 1997).

3. Results

Selection of RNAs Exported in the Presence of M-protein.

Using M protein as an inhibitor of Ran/RCC1 dependent nucleo-cytoplasmic transport in *X. laevis* oocytes, we selected RNAs that are capable of being exported by an alternative pathway. A combinatorial library of sequences comprising 20 nucleotides inserted into a shortened version of U1 RNA (C. Grimm, et al., supra, 1997 and Tuerk and Gold, *Science* 249:505–510, 1990. Both of these are hereby incorporated by reference.) was injected into nuclei of oocytes containing M protein (M oocytes). Exported RNAs were isolated from the cytoplasm and amplified to produce templates for the subsequent round of selection.

After twelve rounds of selection over 60% of the injected RNAs were in the cytoplasm within two hours of injection (FIG. 1A). This mixture of molecules was then subjected to four rounds of counter-selection (nuclear retention at 0° C.) to remove RNAs whose export was by diffusion rather than by active transport. After two additional rounds of selection for export in the presence of M protein, individual cDNAs were cloned and sequenced. Three "winner sequences" predominated among the selected RNAs. Almost half of the clones, represented by clone ET-202, had the same sequence; two other clones (ET-208 and ET-201) each accounted for about a quarter of the total.

FIG. 1A and B diagrams the results of experiments designed to identify selection of RNAs containing nuclear export elements (NEEs). FIG. 1A shows enrichment of injected RNA pools for RNAs containing NEEs. The percentage of exported RNAs at 2 hours (rounds 1–12 and 17–18) or 24 hours (rounds 13–16) after nuclear injection was calculated as [C/(N+C)]×100. Rounds of selection are indicated at the bottom. Filled bars: selection in presence of M protein, open bars: counter-selection on ice. FIG. 1B shows sequences of ET-RNAs (Exported RNAs) after 18 rounds of selection. Shaded box: randomized region (N20). Dots: Nucleotides that were mutated in one isolate of that particular group of ET-sequences. (Δ) nucleotides that were deleted from the fixed sequence during the selection procedure. Arrows indicate the 3+ ends of the primers used for reverse transcription and PCR.

As expected, individual RNAs transcribed from the cloned cDNAs, such as ET-202 RNA, were exported very efficiently in both control and M oocytes. The addition of an $m^7G$-cap to the normally uncapped RNAs was without effect on export. A dimeric version of ET-202 RNA (ET-202/di) was also exported both in the presence and absence of M protein, further ruling out diffusion of a small RNA as an explanation for the appearance of this RNA in the cytoplasm. As described above, export of $m^7G$-capped U1 was blocked by M protein. Coinjected U3 or U6 RNAs served as controls for the accuracy of nuclear injection and nucleocytoplasmic fractionation in this and all other experiments (M.P. Terns, et al., supra, 1995).

Data-base searches failed to detect natural RNAs with sequences strongly homologous to those in the selected RNAs. Probing of the ET-202 RNA structure by enzymatic digestions and chemical modifications suggested the existence of extensive stem-loops and of several tertiary interactions stabilized by $Mg^{2+}$; however, no common secondary structure among the selected RNAs was predicted by computer analysis. When variants of ET-202, generated by error prone PCR, were tested for export efficiency, no specific nucleotide or sequence could be identified as being essential for export. These results suggests that the efficient transport of ET-202 RNA is mediated by the RNA structure rather than the RNA sequence.

Factors Associated With the Selected RNAs

To determine if export of ET-202 RNA depended on factors used by other RNAs, we injected nuclei of control oocytes with mixtures containing labeled RNAs and unlabeled competitors. When present in high amounts, unlabeled ET-202 RNA acted as competitor of its own export, demonstrating that export of this RNA requires a saturable factor(s). In addition, both ET-208 RNA and the small cytoplasmic hY1 RNA competed for export of ET-202 RNA, showing that these three RNAs interacted with a common factor(s). The destabilization of ET-202 RNA upon blockage of its export by competitor RNA may result either from inherent instability of the RNA in the nucleus or from removal of stabilizing proteins. Since unlabeled ET-202 RNA did not block export of ET-208 RNA, the latter RNA probably can utilize an alternative export pathway.

The pathways for export of the selected ET-RNAs and tRNAs share several features such as resistance to inhibition by M protein. However, neither ET-202 nor tRNA interfered with export of the other, indicating that these RNAs do not share factor(s) for their export, or that such a factor(s) is not limiting. Also, the lectin wheat germ agglutinin (WGA) inhibits export of tRNA but not that of ET-202 RNA. Thus, several transport pathways must exist that are insensitive to inhibition by M protein.

Enhanced Export of Chimeric RNAs Containing Selected Sequences.

Because of the efficiency of export of ET-202 and ET-208, we asked if these sequences could act as NEEs for other RNAs that ordinarily are not exported, or only poorly so. We made several chimeric RNAs containing both a selected ET-sequence and normal cellular RNA sequences. All of these chimeras were exported very efficiently in the absence of M protein. For example, U6 RNA normally is retained in nuclei, but most of the chimeric U6/ET-202 RNA appeared in the cytoplasm within one hour of injection into oocyte nuclei. Likewise, ApppG- capped versions of U2 small nuclear RNA (U2 snRNA), a truncated variant of U1 snRNA (U1124 RNA) and adenovirus major late pre-mRNA (AdML) are exported inefficiently on their own, but all of these RNAs were exported very rapidly when they were part of chimeric molecules containing ET-202 or ET-208 sequences.

The enhanced export of chimeric molecules probably utilizes the pathways of the selected sequences, since it can be competed by the homologous selected ET-RNA and does not occur if the chimeric RNA contains either an antisense version of the RNA or sequences from an early round (round 2) of selection. In RNAs containing the U2 RNA sequences, export was efficient regardless of the location of the selected RNA. Thus, the selected RNA sequences confer on the poorly exported non-selected RNAs the ability to use alternate, efficient export pathways.

Nuclear Immobilization of Selected Sequences in Chimeric RNAs.

Unexpectedly, export of the chimeric RNAs was greatly inhibited in the presence of M protein. Therefore, the non-selected sequences apparently contain cis-acting structures that do not allow export of the selected RNAs from the nucleus. If the blockage of export is due to binding of the chimeric RNAs to nuclear structures, these sites must have a very high capacity, as the chimeras were not released by injection of as much as 5.5 pmol competitor RNA. This inhibition of ET-NEE function is detectable only in the presence of compounds such as M protein or mAb 414, both of which also block protein import. We refer to it as "immobilization", to distinguish it from saturable retention that is mediated by sequence-specific RNA binding factors such as La.

A very wide range of sequences can lead to immobilization of the ET-RNA sequences in the presence of M protein. Even a random RNA sequence from the pGEM42 vector led to blockage of export in the presence of M protein. Also, inhibition of export was conferred on the selected RNAs by sequences that are normally exported in the absence of M protein, such as $m^7$G-capped U2 snRNA. Because sensitivity to export inhibition by M protein is conferred by sequences introduced into the selected RNAS, it is possible that the non-selected sequences bind to nuclear structures that block export.

4. Discussion

The results presented here show that when Ran-dependent transport is inhibited RNAs containing functional nuclear export signals (NEEs) are retained in nuclei by a low specificity and high capacity system.

RNAs are actively exported if they contain signals that direct them out of the nucleus and if they do not contain signals for retention within the nucleus. Thus, when we selected RNAs for their ability to be exported in the presence of VSV M protein we required that the RNAs contain cis-acting elements capable of directing export, and that they be devoid of sequences that would lead to their immobilization and retention even when the Ran-dependent transport system is inactive. The selected ET-202 or ET-208 RNAs can supply nuclear export elements (NEEs) to RNAs that otherwise lack export signals, such as U6 RNA. The resulting chimeric RNAs are exported via the pathway normally used for the export of the selected RNAs. The added sequences in the chimeric RNAs must be responsible for the lack of export of the ET-202 and ET-208 RNA sequences.

We claim:

1. A method of inhibiting transport of RNA and proteins between the nucleus and cytoplasm of a cell comprising the step of exposing an intact cell in vitro to a sufficient quantity of vesicular stomatitis virus (VSV) matrix protein (M protein) such that the transport of RNA and proteins through the nuclear envelope of the cell is impeded.

2. The method of claim 1 wherein M protein is obtained by translation of M protein mRNA, wherein the cell has been pre-incubated with the M protein mRNA.

3. The method of claim 1 wherein the M protein is obtained by extraction from VSV or a recombinant bacterial host cell.

4. A method of inhibiting transport of RNA and proteins between the nucleus and cytoplasm of a cancer cell comprising the step of exposing a cancer cell in vitro to a sufficient quantity of vesicular stomatitis virus M protein such that the transport of RNA and proteins through nuclear envelope of the cell is impeded.

5. The method of claim 4 wherein the M protein is obtained from translation of M protein mRNA, wherein the cell has been preincubated with the M protein mRNA.

6. The method of claim 4 wherein the M protein is obtained by extraction from VSV or a recombinant bacterial host cell.

7. A method of inhibiting transport of RNA and proteins between the nucleus and cytoplasm of a cell comprising the steps of (a) analyzing the vesicular stomatitis virus M protein to determine a smaller fragment that retains the ability to inhibit nucleo-cytoplasmic transport, wherein sized fragments of the protein are compared to determine which segments of the protein can be deleted without loss of transport inhibition; and (b) exposing a cell in vitro to a sufficient quantity of the smaller fragment such that transport of RNA and proteins across the nuclear envelope of the cell is impeded.

8. A method of inhibiting export of nucleic acids from the nucleus to the cytoplasm of a cell comprising the step of exposing the cell in vitro to a sufficient quantity of vesicular stomatitis virus M protein such that the export of said nucleic acids through the nuclear envelope of the cell is impeded.

9. A method of inhibiting the import of proteins or RNA-protein complexes from the nucleus to the cytoplasm of a cell comprising the step of exposing the cell in vitro to a sufficient quantity of the vesicular stomatitis virus M protein such that the import of proteins or RNA-protein complexes through the nuclear envelope of the cell is impeded.

10. A method of selecting a nuclear export element, comprising the steps of (a) exposing a cell in vitro to a sufficient amount of M protein so that export of RNA between the nucleus and cytoplasm is inhibited; and (b) selecting an RNA molecule that is exported in the presence of M protein and examining the molecule for the presence of a nuclear export element.

11. A chimeric RNA comprising a nuclear export element as shown in any one of SEQ ID NOs: 3–8 and a target RNA sequence, wherein the target RNA sequence is not natively attached to the export element.

12. The chimeric RNA of claim 11, wherein the nuclear export element is selected from the group consisting of residues 14–33 of SEQ ID NO:3, residues 10–29 of SEQ ID NO:4, residues 10–29 of SEQ ID NO:5, residues 14–33 of SEQ ID NO:6, residues 11–30 of SEQ ID NO:7, and residues 10–28 of SEQ ID NO:8.

13. The chimeric RNA of claim 11, wherein the nuclear export element is selected from the group consisting of SEQ ID NO:3, SEQ ID NO:4, SEQ ID NO:5, SEQ ID NO:6, SEQ ID NO:7 and SEQ ID NO:8, wherein the nuclear export element sequence has been truncated but still retains nuclear export activity.

14. A chimeric DNA molecule encoding the RNA of claim 11.

15. A host cell containing the chimeric RNA of claim 11.

16. A method of directing the nuclear export of a target RNA sequence, comprising the steps of
   (a) synthesizing the chimeric RNA of claim 11, wherein the RNA is contained within a host cell nucleus, and
   (b) allowing the target RNA to be exported to the cytoplasm of the host cell in vitro.

17. A method of inhibiting RNA and protein transport within the nucleus of a cell, comprising the step of exposing an intact cell in vitro to a sufficient quantity of vesicular stomatitis virus M protein such that the transport of RNA and proteins within the nucleus of the cell is impeded.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other ( x i ) SEQUENCE DESCRIPTION: SEQ ID NO:1:

CTCGAGTACT        10

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other ( x i ) SEQUENCE DESCRIPTION: SEQ ID NO:2:

GAATTCGATT TAGGTGACAC TATA        24

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

GGAGAUACCC UGUGAUUAGC AGGGCCUUGC AAAGGUAGG    39

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:4:

GGACCCUGAU UGAGGGCCCU CAUUGCCGCG GUAGG    35

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:5:

GGAGAUACAU UCGACCUCCU AUGCUUUAGG GUAAGG    36

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:6:

GGUGAUACCC UGAGAUUAUC AGGACCUUGA UCGGGUAGG    39

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:7:

GGUACCCUGA CUAAGCGGUG ACCUGCGAUC GGUAGGG    37

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:8:

-continued

GGAGAUAGAU UGCUCUCUCG AUGCUACCGG UAGG 34

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:9:

GGGAUACUUA CCUGGCAGGG GAGAUACCCU GA 32

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:10:

GGUAGUGGGG GACUGCGUUC GCGCUUUCCC CUGAU 35